United States Patent [19]

Prain et al.

[11] Patent Number: 4,904,664
[45] Date of Patent: Feb. 27, 1990

[54] BENZENE COMPOUNDS HAVING TWO PYRIDAZINONE SUBSTITUENTS

[75] Inventors: Hunter D. Prain; Brian H. Warrington, both of Welwyn Garden City, England

[73] Assignee: Smith Kline & French Laboratories Limited, Welwyn Garden City, United Kingdom

[21] Appl. No.: 880,849

[22] Filed: Jul. 1, 1986

[30] Foreign Application Priority Data

Jul. 5, 1985 [GB] United Kingdom ............... 8517051
Mar. 20, 1986 [GB] United Kingdom ............... 8606853

[51] Int. Cl.$^4$ .................. C07D 401/10; A61K 31/50
[52] U.S. Cl. .................................... 514/252; 544/238
[58] Field of Search .............. 544/238, 239; 514/252

[56] References Cited

U.S. PATENT DOCUMENTS

| | | | |
|---|---|---|---|
| 3,845,050 | 10/1974 | Lebkuecher et al. | 544/238 |
| 3,975,388 | 8/1986 | Hakim et al. | |
| 4,088,762 | 5/1978 | Hakim et al. | |
| 4,353,905 | 10/1982 | Sircar et al. | |
| 4,521,415 | 6/1985 | Katakami et al. | 514/252 |
| 4,551,455 | 11/1985 | Hilboll et al. | 514/252 |
| 4,599,332 | 7/1986 | Sircar | 514/247 |
| 4,603,201 | 7/1986 | Takesheba et al. | 544/238 |
| 4,631,279 | 12/1986 | Robertson | 514/247 |
| 4,661,484 | 4/1987 | Okushima et al. | 514/242 |

FOREIGN PATENT DOCUMENTS

| | | |
|---|---|---|
| 75436 | 9/1982 | European Pat. Off. |
| 167995 | 7/1984 | European Pat. Off. |
| 178875 | 10/1984 | European Pat. Off. |
| 0125636 | 11/1984 | European Pat. Off. |
| 175363 | 6/1985 | European Pat. Off. |
| 2515175 | 4/1983 | France |
| 2094302 | 9/1982 | United Kingdom |

OTHER PUBLICATIONS

G. R. Brown et al., J. Chem. Soc. Chem. COmmun., 1984, 1373.
Abstract and Claims for EP89,650.
Physicians Desk Reference (1987), p. 643–645.

Primary Examiner—Mark L. Berch
Attorney, Agent, or Firm—Charles M. Kinzig; Janice E. Williams; Alan D. Lourie

[57] ABSTRACT

The invention relates to pyridazinone derivatives which have inotropic, vasodilator and bronchodilator activity. The compounds of the invention are described by formula (I):

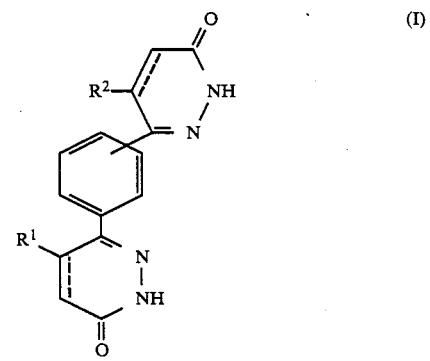

wherein:
  $R^1$ is hydrogen or methyl;
  $R^2$ is hydrogen or methyl; --- and === represent double or single bonds; and the benzene ring is para- or meta-substituted; and pharmaceutically acceptable salts thereof.

18 Claims, No Drawings

BENZENE COMPOUNDS HAVING TWO PYRIDAZINONE SUBSTITUENTS

The present invention relates to benzene derivatives and in particular to such compounds having two 6-oxo-1,6-dihydropyridazin-3-yl substituents and 6-oxo-1,4,5,6-tetrahydro analogues thereof. This invention further relates to pharmaceutical compositions containing them and a method of stimulating cardiac activity by administering them. The compounds of this invention are phosphodiesterase type III inhibitors and are of use in combatting such conditions wherein such inhibition is thought to be beneficial. Thus the compounds of this invention are positive inotropic agents and vasodilators, and are therefore of value in combatting cardiovascular disease, in particular congestive heart failure. In addition the compounds of this invention inhibit platelet aggregation and therefore have an antithrombotic effect. Furthermore the compounds of this invention are bronchodilators and are therefore of use in combatting chronic obstructive lung diseases such as asthma and bronchitis. The major utility of the compounds of this invention is in the treatment of congestive heart failure, and for such treatment the compounds have a very desirable profile of activity.

Congestive heart failure is traditionally treated with cardiac glycosides, for example digoxin and digitoxin, and sympathomimetic agents. The glycosides have pronounced toxic effects with a low therapeutic index. The sympathomimetic agents generally do not have the desired profile of activity and are not orally effective. Amrinone is a marketed compound of interest that is reported to be an inotropic agent. This has an undesirable profile of side-effects when administered orally and development is being restricted to other modes of administration. Clearly there is a continuing need for orally active inotropic agents that have a good therapeutic profile.

Accordingly the present invention provides compounds of the formula (I):

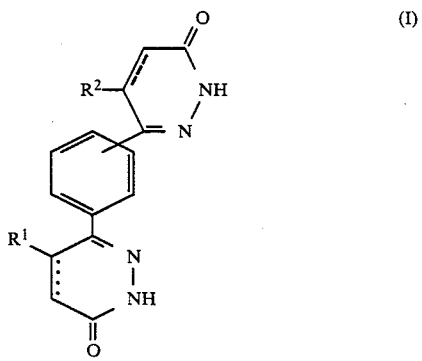

and pharmaceutically acceptable salts thereof, wherein
$R^1$ is hydrogen or methyl;
$R^2$ is hydrogen or methyl;
..... and ---- represent double or single bonds; and the benzene ring is para- or meta-substituted.

Suitably $R^1$ and/or $R^2$ are hydrogen. Suitably $R^1$ and/or $R^2$ are methyl.

Suitably $R^1$ and $R^2$, ..... and ---- are such that the molecule is symmetrical.

Preferably ..... is a single bond and $R^1$ is hydrogen or methyl.

Preferably ---- is a double bond and $R^2$ is hydrogen.
Preferably the benzene ring is para substituted.
Particular compounds of this invention are:
1,4-bis(6-oxo-1,6-dihydropyridazin-3-yl)benzene,
1,4-bis(6-oxo-1,4,5,6-tetrahydropyridazin-3-yl)benzene,
1,4-bis(4-methyl-6-oxo-1,4,5,6-tetrahydropyridazin-3-yl)benzene,
1,4-bis(4-methyl-6-oxo-1,6-dihydropyridazin-3-yl)benzene,
1,3-bis(6-oxo-1,6-dihydropyridazin-3-yl)benzene,
6-[4-(4-methyl-6-oxo-1,4,5,6-tetrahydropyridazin-3-yl)phenyl]pyridazin-3(2H)-one, and
6-[4-(6-oxo-1,4,5,6-tetrahydropyridazin-3-yl)phenyl]pyridazin-3(2H)-one.
and pharmaceutically acceptable salts thereof.

The compounds of the invention are depicted as pyridazin-3(2H)-ones and dihydropyridazin-3(2H)-ones, but of course the present invention covers all tautomeric forms thereof, for example the dihydropyridazinol and pyridazinol forms. Furthermore the present invention covers all the optical isomeric forms of the compounds of the formula (I) which contain 4-methyl-6-oxo-1,4,5,6-tetrahydropyridazin-3-yl groups in the diastereoisomeric, racemic and separated forms. In particular when $R^1$ is methyl and ..... is a single bond, the (R) isomer of a compound of formula (I) is preferred. Compounds of the formula (I) which contain 4-methyl-6-oxo-1,4,5,6-tetrahydropyridazin-3-yl groups generally have higher intrinsic activity than their desmethyl analogues however the latter compounds might be preferred because they do not exhibit optical isomerism and therefore difficulties associated with racemic mixtures e.g. as described by E. J. Ariëns (Trends in Pharmacological Sciences, 200–205, (1986)) would be avoided.

The compounds of the formula (I) can form pharmaceutically acceptable acid addition salts with acids such as hydrochloric, hydrobromic, sulphuric, phosphoric, methanesulphonic and ethanesulphonic acids. Compounds of the formula (I) in which ..... and/or ---- are double bonds can also form pharmaceutically acceptable salts with metal ions, such as alkali metals for example sodium and potassium or alkaline earth metals for example calcium and magnesium.

In order to use a compound of the formula (I) or a pharmaceutically acceptable salt thereof for the treatment of humans and other mammals it is normally formulated in accordance with standard pharmaceutical practice as a pharmaceutical composition.

Compounds of formula (I) and their pharmaceutically acceptable salts may be administered in standard manner for the treatment of the indicated diseases, for example orally, parenterally, trans-dermally, rectally, via inhalation or via buccal administration.

Compounds of formula (I) and their pharmaceutically acceptable salts which are active when given orally or via buccal administration can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

A typical suppository formulation comprises a compound of formula (I) or a pharmaceutically acceptable salt thereof which is active when administered in this way, with a binding and/or lubricating agent, for example polymeric glycols, gelatins, cocoa-butter or other low melting vegetable waxes or fats.

Typical transdermal formulations comprise of a conventional aqueous or non-aqueous vehicle, for example a cream, ointment, lotion or paste or in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane.

Preferably the composition is in unit dosage form, for example a tablet, capsule or metered aerosol dose, so that the patient may administer to himself a single dose.

Each dosage unit for oral administration contains suitably from 0.001 mg/Kg to 3 mg/Kg, and preferably from 0.01 mg/Kg to 1.5 mg/Kg, and each dosage unit for parenteral administration contains suitably from 0.001 mg/Kg to 1 mg/Kg, of a compound of formula (I) or a pharmaceutically acceptable salt thereof calculated as the free base.

The daily dosage regimen for oral administration is suitably about 0.01 mg/Kg to 12 mg/Kg, of a compound of formula (I) or a pharmaceutically acceptable salt thereof calculated as the free base. The daily dosage regimen for parenteral administration is suitably about 0.001 mg/Kg to 4 mg/Kg, for example about 0.01 mg/Kg to 1 mg/Kg, of a compound of the formula (I) or a pharmaceutically acceptable salt thereof calculated as the free base. The active ingredient may be administered from 1 to 4 times a day, sufficient to increase cardiac output. The compositions of the present invention have positive inotropic activity and vasodilator activity and are of use in the treatment of cardiovascular diseases which can be treated by compounds having either or both of these activities, One such disease condition is congestive heart failure. The compounds of the invention are also bronchodilators and are useful in chronic obstructive lung disease for example asthma and bronchitis. Such conditions can be treated by administration orally, rectally, parenterally or by inhalation. For administration by inhalation dosages are controlled by a valve, are administered as required and for an adult are conveniently in the range 0.1–5.0 mg of a compound of the formula (I) or a pharmaceutically acceptable salt thereof.

The compounds of this invention may be co-administered with other pharmaceutically active compounds, for example in combination, concurrently or sequentially. Conveniently the compounds of this invention and the other active compound or compounds are formulated in a pharmaceutical composition. Examples of compounds which may be included in pharmaceutical compositions with the compounds of the formula (I) are vasodilators for example hydralazine, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, cardioglycosides for example digoxin and digitoxin, calcium antagonists for example verapamil and nifedipine, diuretics such as thiazides and related compounds for example bendrofluazide, chlorothiazide, chlorothalidone, hydrochlorothiazide, and other diuretics for example frusemide and triamterene, and sedatives for example nitrazepam, flurazepam and diazepam.

The compounds of the formula (I) or pharmaceutically acceptable salts thereof, may be prepared by a process which comprises reacting a compound of the formula (II):

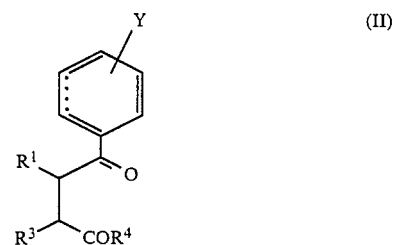

where
Y is

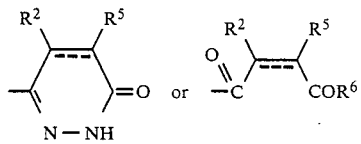

where $R^2$ is hydrogen or methyl, $R^5$ is hydrogen or $R^5$ can be OH when ----- is a single bond, $R^6$ is OH, $OR^7$ or $NH_2$, where $R^7$ is $C_{1-4}$alkyl;

$R^1$, ..... and ---- are as defined for formula (I), and $R^3$ is hydrogen or $R^3$ can be OH when ..... is a single bond, and $R^4$ is OH, $OR^7$, or $NH_2$ where $R^7$ is $C_{1-4}$alkyl;

with hydrazine or a chemical equivalent thereof, and where Y is

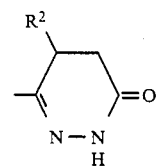

and/or ..... is a single bond, followed by optional dehydrogenation,
or when Y is

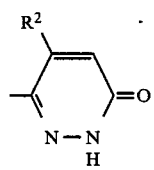

and/or ···· is a double bond, followed by optional hydrogenation.

when $R^3$ or $R^5$ are OH an additional step of dehydration e.g. (treatment with an acid e.g. hydrochloric acid in acetic acid) is carried out.

Preferably $R^4$ and $R^6$ are both OH.

By a chemical equivalent of hydrazine we mean hydrazine hydrate, hydrazine ethanolate or a similar solvate. Preferably hydrazine is used in the form of hydrazine hydrate.

Preferably an excess of hydrazine is used, for example from 1 to 5 molar equivalents for each pyridazinone group to be formed. Preferably the reaction is carried out in the presence of a solvent for example water, $C_{1-4}$alkanols, acetic acid and aqueous mixtures thereof. Preferably the reaction is carried out at an elevated temperature, for example 60°–110° C., preferably at the reflux temperature of the reaction mixture.

Methods of dehydrogenation for dihydropyridazinones include treatment with m-nitrobenzenesulphonic acid and a base, or with bromine in acetic acid.

Methods of hydrogenated for pyridazinones include those described by G. R. Brown et al, J. Chem. Soc. Chem. Commum. 1984, 1373 and particularly include zinc and acetic acid.

The general processes for preparing the compounds of formula (I) and intermediates therefor are outlined in Scheme 1. For convenience para-substituted compounds are shown and analogous processes can be used to prepare the meta analogues.

SCHEME 1

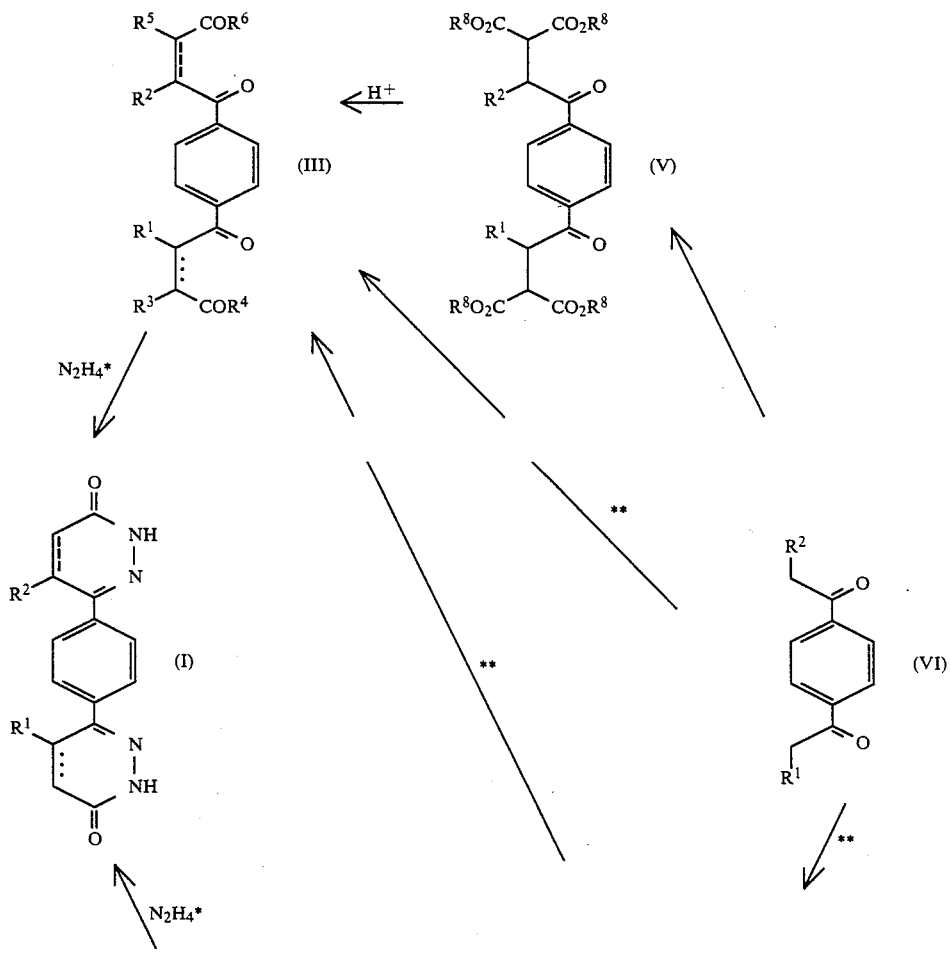

-continued
SCHEME 1

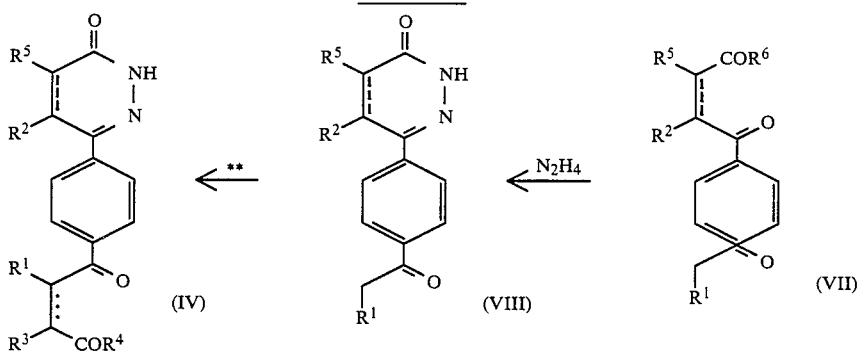

*followed by optional dehydrogenation or hydrogenation
**reaction with an alkyl bromoacetate or Mannich procedure if ⋯ or ≡ to be introduced are single bonds or reaction with glyoxylic acid if ⋯ or ≡ to be introduced are double bonds.

The intermediates of formula (II) in which Y is

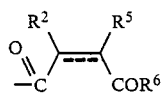

(which are shown as formula (III) can be prepared from diacylbenzene compounds of formula (VI) in which $R^1$ and $R^2$ are as defined for formula (I) by the following general routes:

(a) For compounds in which ____ and ⋯ are single bonds, $R^3$ and $R^5$ are hydrogen and $R^4$ and $R^6$ are both OH, by bromination and reaction with the sodium derivative of a dialkyl malonate (preferably diethyl malonate) to give a compound of formula (V) in which $R^8$ is $C_{1-4}$alkyl which is then hydrolysed and decarboxylated. Suitably the bromination is carried out using bromine or N-bromosuccinimide in a suitable solvent, preferably using bromine in acetic acid. Preferably the hydrolysis is carried out under aqueous acidic conditions.

(b) For compounds in which ____ and ⋯ are single bonds, $R^3$ and $R^5$ are hydrogen and $R^4$ and $R^6$ are $OR^7$, by formation of a sodium salt of the compound of formula (VI) and reaction with an alkyl bromacetate. Suitably the sodium salt is formed by reaction with sodium hydride. Preferably the alkyl bromoacetate is ethyl bromoacetate.

(c) For compounds in which ____ and ⋯ are single bonds, $R^3$ and $R^5$ are hydrogen and $R^4$ and $R^6$ are both OH or $NH_2$, by reaction of a compound of formula (VI) with a Mannich reagent to give an intermediate of formula (IX) in which R is $C_{1-4}$alkyl, followed by optional quaternisation to give an intermediate of formula (X) in which X is a halide or methylsulphate, treatment with potassium cyanide to give a nitrile of formula (XI) and hydrolysis.

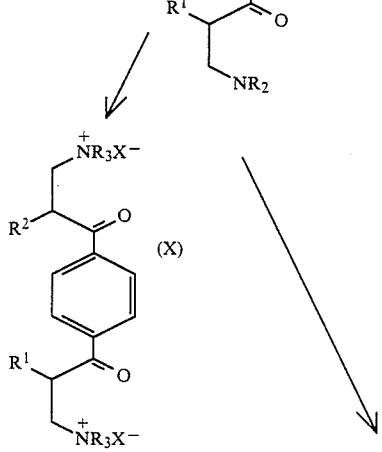

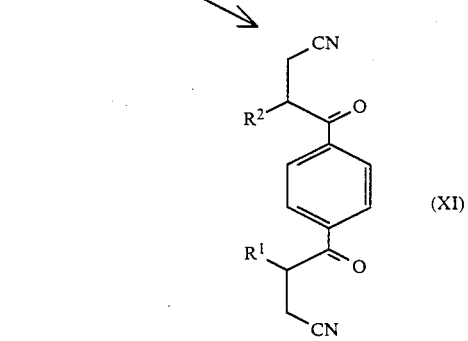

Examples of Mannich reagents are dimethylamine and formaldehyde, and bis(dimethylamino)methane. Preferably a slight excess of Mannich reagent is used, for example 1.3 molar equivalents for each Mannich group to be introduced. Preferably the reaction is carried out in the presence of an inert organic solvent for example $C_{1-4}$alkanols. Preferably the reaction is carried out at an elevated temperature, for example 60°–100° C., preferably at the reflux temperature of the reaction mixture.

Preferably quaternisation is carried out by reaction with an alkyl halide or a dialkyl sulphate.

Preferably the treatment with potassium cyanide is carried out in the presence of a solvent, for example water, $C_{1-4}$alkanols, acetic acid and aqueous mixtures thereof.

The acids (III) in which $R^4$ and $R^6$ are OH can be prepared by hydrolysis of the nitriles (XI), using aqueous acids or bases, carried out at elevated temperatures, e.g. 100° C.

The amides (III) in which $R^4$ and $R^6$ are $NH_2$ are prepared by hydrolysis of the nitriles (XI), using concentrated acids, carried out at moderate temperatures.

The sequence of reaction with a Mannich reagent and optional quaternisation followed by reaction with potassium cyanide and hydrolysis is hereinafter referred to as the 'Mannich procedure'.

(d) For compounds in which ____ and .... are double bonds or single bonds when $R^3$ and $R^5$ are OH, and $R^4$ and $R^6$ are OH, by reaction with glyoxylic acid or a chemical equivalent thereof. By a chemical equivalent of glyoxylic acid we means a solvate such as the hydrate or a combination of reagents which can generate glyoxylic acid in situ e.g. a mixture of tartaric acid and sodium metaperiodate.

Preferably a compound of formula (VI) is fused with glyoxylic acid hydrate and the product is dissolved in aqueous ammonia to pH 10. Preferably a slight excess of glyoxylic acid is used, for example 1.2–1.4 molar equivalents for each acid group to be introduced.

Variations on the above reactions are possible, for example the compound of formula (VI) can be reacted with one molar equivalent of an alkyl bromoacetate or glyoxylic acid or one molar equivalent of a Mannich reagent in the Mannich procedure to give a compound of formula (VII), which can be reacted with hydrazine to give a compound of formula (VIII). In other variations compounds of formulae (VII) and (VIII) can be reacted with one molar equivalent of an alkyl bromoacetate or glyoxylic acid to give the appropriate compounds of formulas (III) and (IV), or the compounds of formulas (VII) and (VIII) can be reacted with one molar equivalent of a Mannich reagent in the Mannich procedure followed by subsequent processing to give compounds of the formulas (XIV) and (XV) respectively:

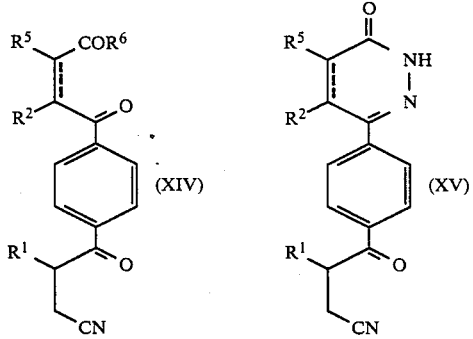

where $R^1$, $R^2$, $R^5$, $R^6$ and ____ are as defined for a compound of the formula (II).

The compounds of the formulas (XIV) and (XV) can be hydrolysed to the corresponding compounds of the formulas (III) and (IV) in an analogous manner to that hereinbefore described for compounds of the formula (XI).

In other alternative procedures compounds of formula (VI) can be reacted with one molar equivalent of bromine followed by reaction with sodium dialkylmalonate, hydrolysis and decarboxylation and the second acyl group treated with one molar equivalent of an alkyl bromoacetate or glyoxylic acid or subjected to the Mannich procedure as generally described above.

Other variations on the scheme are also possible, for example intermediates (III), (IV), (VII) and (VIII) can be subjected to optional dehydrogenation or hydrogenation.

The diacylbenzene compounds of formula (VI) can be prepared by oxidising compounds of formula (XII) in which $R^1$ and $R^2$ are as defined for formula (I), for example with chromium trioxide in acetic anhydride:

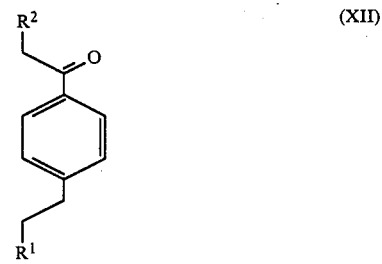

An alternative process for preparing the intermediates of formula (VIII) in which ____ is a double bond is by oxidation of a compound of formula (XIII):

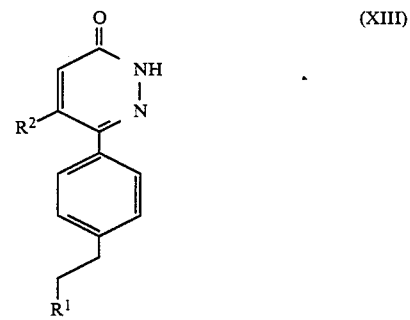

in which $R^1$ and $R^2$ are as defined in formula (I). Preferably this oxidation is carried out using chromium trioxide, particularly preferably in the presence of acetic anhydride.

The intermediates of formula (XIII) can be prepared by reacting a compound of formula (XII) with glyoxylic acid and hydrazine or chemical equivalents thereof. Preferably a compound of formula (XII) is fused with glyoxylic acid hydrate and the product is dissolved in aqueous ammonia to pH 10 and reacted with hydrazine at an elevated temperature. Preferably a slight excess of glyoxylic acid is used, for example 1.4 molar equivalents per mole of starting material of formula (XII).

Pharmaceutically acceptable acid addition salts of the compounds of the formula (I) may be prepared from the corresponding base of the compounds of the formula (I) in conventional manner. For example the base may be reacted with an acid in a $C_{1-4}$alkanol, or an ion-exchange resin may be used. The salts of the compounds of the formula (I) may be interconverted using ion-exchange resins. Non-pharmaceutically acceptable salts are therefore of use as they can be converted to pharmaceutically acceptable salts.

Pharmaceutically acceptable base addition salts of the compounds of the formula (I) in which .... and/or ____ are double bonds may be prepared by standard methods, for example by reacting a solution of the compound of the formula (I) in which .... and/or ____ are double bonds with a solution of the base.

The optical isomers of compounds of formula (I) which contain 4-methyl-6-oxo-1,4,5,6-tetrahydropyridazin-3-yl groups may be separated by passage of racemic compound over a chiral phase chromatography column.

The following biological test methods, data and Examples serve to illustrate this invention.

Cardiac Stimulant Activity—In vitro

The compounds of formula (I) and their pharmaceutically acceptable salts are tested for cardiac stimulant activity following a procedure based on that of S. C. Verma and J. H. McNeill (J. Pharm. & Exp. Therapeutics, 200, 352–362 (1977)). Guinea pigs (500–700 g) of either sex are sacrificed and the hearts are quickly removed and transferred to a dissecting dish containing oxygenated bathing fluid. While in the bathing medium, the right ventricle is cut into two strips. The strips are each suspended in a 50 ml bath containing Krebs Henseleit solution at 37° C., and the bath is bubbled with 95% oxygen and 5% carbon dioxide. The ventricular strips are electrically stimulated at a frequency of 1.0 Hz, at double the threshold voltage. A resting tension of 1.0 g is applied to the strips and the tension is kept constant by readjustment during an equilibration period of 60 minutes. The bathing fluid is frequently changed during this period. When a steady base line is obtained, a compound under test is added to the bathing fluid and a cumulative concentration response curve is plotted. The compounds for use in the present invention which were tested gave a 50% ($EC_{50}$) increase in the force of contraction of the ventricular strips at concentrations in the bathing fluid of less than $10^{-4}$ molar, thus showing that they have activity as positive inotropic agents.

In the above test method the compound of Example 1 gave an $EC_{50}$ value of $0.9 \times 10^{-6}$ M. In comparison amrinone gave a value of $15 \times 10^{-6}$ M.

Cardiac Stimulant Activity—In vivo (Anaesthetised Cats)

In anaesthetised cats pretreated with a ganglion blocker (pempidine) and propranolol, the compounds of the Examples caused sustained increases in left ventricular dp/dt max (this is an index of left ventricular contractility) when administered intravenously. The dose to increase left ventricular dp/dt max by 50% is given as the $ED_{50}$.

| Compound of Example | $ED_{50}$ (micromol/kg) | Relative # Duration |
| --- | --- | --- |
| 1 | 0.04 | *** |
| 2 | 0.55 | *** |
| 3 | 0.06 | *** |
| 5 | 3.16 | *** |
| 6 | 0.02 | *** |

| Compound of Example | $ED_{50}$ (micromol/kg) | Relative # Duration |
| --- | --- | --- |
| Amrinone | 5.6 | * |

Relative duration was estimated in the anaesthetised cats following the i.v. administration:
***long
*short Minimal changes in blood pressure or heart rate were observed.

Inhibition of Phosphodiesterases

Three peaks of cyclic nucleotide phophodiesterase activity [PDE (Peak I), PDE (Peak II) and PDE (Peak III)] from cat heart were separated by chromatography on DEAE-Sepharose CL-6B (Diethylaminoethyl Cellulose with a bead size of 45–165 microns). Sepharose is a trademark of Pharmacia Fine Chemicals Inc. The high-speed supernatant from a cat heart homogenate (2 g tissue in 20 ml 20 mM PIPES (Piperazine-N-N'-bis[2-ethanesulfonic acid]), 50 mM Na acetate, pH 6.5) was applied to a $15 \times 1.5$ cm column of DEAE-Sepharose equilibrated with the homogenisation buffer. The PDE activities were eluted with a gradient of 0.05–1M Na acetate in 20 mM PIPES. There were three major peaks which had the following characteristics:

| PDE (Peak I) - eluted at 0.15 M Na acetate | | | |
| --- | --- | --- | --- |
| Substrate | 50 µg/ml calmodulin (+ = added) | Km (µM) | Relative $V_{max}$ |
| cyclic AMP | — | 0.5 | 1 |
| cyclic GMP | — | 1.8 | 1.1 |
| cyclic AMP | + | 0.7 | 6.3 |
| cyclic GMP | + | 1.4 | 7.2 |

| PDE (Peak II) - eluted at 0.3 M Na acetate | | |
| --- | --- | --- |
| Substrate | Km (µM) | Relative $V_{max}$ |
| cyclic AMP | 6 | 1 |
| cyclic GMP | 28 | 0.2 |

| PDE (Peak III) - eluted at 0.5 M Na acetate | | |
| --- | --- | --- |
| Substrate | Km (µM) | Relative $V_{max}$ |
| cyclic AMP | 0.6 | 1 |
| cyclic GMP | 2.9 | 0.4 |

PDE (Peak I) has high affinity for cyclic AMP and cyclic GMP and is characterised by an activation by $Ca^{2+}$/calmodulin complex.

PDE (Peak II) demonstrates relatively low affinities for both cyclic AMP and cyclic GMP and is not affected by $Ca^{2+}$/calmodulin complex.

PDE (Peak III) has high affinity for cyclic AMP. It can also hydrolyse cyclic GMP though the preferred substrate is cyclic AMP. This activity is also insensitive to $Ca^{2+}$/calmodulin activation.

Enzyme assay

The enzyme was assayed by incubation at 37° for 4–30 min in 50 mM Tris, 5 mM $MgCl_2$, pH 7.5 with [3-H]cyclic nucleotide ($4 \times 10^5$ disintegrations $min^{-1}$) and [14-C] nucleotide 5' monophosphate ($3 \times 10^3$ disintegrations $min^{-1}$). The assay was stopped by boiling, and the [3-H] 5' monophosphate product separated from substrate on boronate columns (Davis, C. W. and Daly, J. W. (1979) J. Cyclic Nucleotide Res., 5, 65–74). The reaction mixture was diluted with 0.5 ml 100 mM HEPES (N-2-Hydroxyethylpiperazine-N'-2-ethanesulfonic acid), 100 mM NaCl, pH 8.5, and applied to the column. The column was extensively washed with the same buffer, and the 5' nucleotide eluted with 6 ml 0.25M acetic acid. The recovery of product as judged by [14-C] recovery was approximately 80%. All assays were linear with time of incubation and concentration of enzyme over the range used in these experiments.

Calculation of $IC_{50}$ values $IC_{50}$ values (the concentration of inhibitor required for 50% inhibition of activity) were obtained for PDE (Peak III) by incubation of the enzyme 1 μM cyclic AMP, and a range of inhibitor concentrations from $0.1 \times IC_{50}$ to $100 \times IC_{50}$.

| Compound of Example | $IC_{50} \times 10^{-6}M$ |
| --- | --- |
| 1 | 0.33 |
| 2 | 0.64 |
| 3 | 0.11 |
| 4 | 37.5 |
| 5 | 3.9 |
| 6 | 0.07 |
| Amrinone | 51.8 |
| Milrinone | 2.2 |

The invention is illustrated but in no way limited by the following Examples.

Vasodilator Activity

The compounds of the Examples were tested in autoperfused anaesthetised cat hind quarters (autoperfused at constant blood flow). The i.v. dose to decrease hindquarters perfusion pressure (vasodilatation) by 15% is given as the $ED_{15}$.

| Compound of Example | $ED_{15}$ (μm/kg) |
| --- | --- |
| 2 | 0.12 |
| 3 | 0.04 |
| 5 | 3.23 |
| 6 | 0.01 |

Bronchodilatation—In vivo

Male guinea-pigs of the Dunkin Hartley strain (500–600 g) were anaesthetised with Sagatal (pentobarbital sodium) (60 mg/kg i.p.). Airway resistance was measured using a modification of the classical Konzett-Rossler technique (Versuchsanordnung zu Untersuchungen an der Bronchialmuskulatur. Naunyn-Schmiedebergs Arch. Exp. Path. Pharmak., 195: pp 71–74, (1940)). A dose of histamine which gave approximately 150% increase in airway resistance was selected for i.v. administration. Bolus doses of the compound of Example 6 were administered (i.v.) on minute before the histamine challenge (n=1).

The compound of Example 6 reduced the histamine-induced bronchoconstriction. The dose of the compound of Example 6 which would reduce the histamine bronchoconstriction by 50% ($ED_{50}$) (calculated by interpolation of data obtained) was determined to be $3.3 \times 10^{-8}$ mol/kg, demonstrating in-vivo anti-bronchoconstrictor activity.

EXAMPLE 1

1,4-Bis(6-oxo-1,6-dihydropyridazin-3-yl)benzene,

A mixture of 1,4-diacetylbenzene (8.11 g) and glyoxylic acid monohydrate (13.18 g) was stirred and heated at 110° C. for 20 minutes. The semi-solid obtained was dissolved in aqueous ammonia (approx. 25 ml) to pH 10 and the solution filtered. The filtrate was treated with hydrazine hydrate (10 ml), refluxed for one hour, and the precipitated yellow solid (8.43 g) was filtered off.

The crude product was recrystallised from acetic acid/concentrated hydrochloric acid to give pure 1,4-bis(6-oxo-1,6-dihydropyridazin-3-yl)benzene, m.p.>250° C. $\nu$ (nujol); 3340–2000, 1680, 1650, 1593, 835 cm$^{-1}$. $\delta$ (NaOD); 6.98 (2H, d, 5,5'—H$_2$), 7.81 (2H, d, 4,4'—H$_2$), 7.93 (4H, s, phenyl).

EXAMPLE 2

1,4-Bis(6-oxo-1,4,5,6-tetrahydropyridazin-3-yl)benzene (a) 1,4-Bis(3-dimethylamino-1-propionyl)benzene dihydrochloride A mixture of 1,4-diacetylbenzene (8.1 g), paraformaldehyde (4.0 g), dimethylammonium chloride (10.6 g) and concentrated hydrochloric acid (0.2 ml) in ethanol (50 ml) was stirred and refluxed for 3 hours. The pale yellow solution obtained was poured into dry acetone (200 ml) and the crude product (14.8 g; m.p. 197° C. (d)) filtered off. Recrystallisation from ethanol/acetone gave 12.3 g (70%) of pure 1,4-bis(3-dimethylamino-1-propionyl)benzene dihydrochloride, m.p. 205° C. (d). $\nu$ (nujol); 2700–2300, 1683, 1235, 845 cm$^{-1}$, $\delta$ (D$_2$O); 3.00 (12H, s, —CH$_3$), 3.62 (8H (exchangeable), (m, —CH$_2$—), 8.17 (4H, s, phenyl).

(b) 1,4-Bis(3-cyano-1-propionyl)benzene

A solution of potassium cyanide (5.5 g) in water (30 ml) was added dropwise to a stirred solution of 1,4-bis(3-dimethylamino-1-propionyl)benzene dihydrochloride (7.00 g) in water (70 ml) containing acetic acid (2.5 ml). When addition was complete the mixture was heated at 80° C. for 3 hours. 1,4-Bis(3-cyano-1-propionyl)benzene (3.52 g (72%)) separated as a buff solid and was filtered off and washed with water, m.p. 162°–5° C. $\nu$ (nujol) 2240, 1680, 850 cm$^{-1}$, $\delta$ (DMSOd$_6$) 2.79 (4H, t, 2,2'—H$_2$), 3.53 (4H, t, 3,3'—H$_2$) 8.12 (4H, m, Phenyl).

(c) 1,4-Bis(6-oxo-1,4,5,6-tetrahydropyridazin-3-yl)benzene

A suspension of 1,4-bis(3-cyano-1-propionyl)benzene (3.0 g) in 2N sodium hydroxide (20 ml) was refluxed until all material went into solution (approx. 2 hours). The cooled solution was diluted with water (50 ml), acidified (hydrochloric acid) and the precipitate of crude 1,4-bis(3-carboxy-1-propionyl)benzene (0.72 g) collected. Without further purification, this material was dissolved in 50% aqueous acetic acid (50 ml), treated with hydrazine hydrate (0.26 ml) and the mixture was refluxed for 4 hours. The brown solid obtained by evaporation of the solution, was triturated with dilute sodium hydrogen carbonate solution, filtered off and washed with water. Recrystallisation of the crude product from aqueous acetone gave pure 1,4-bis(6-oxo-1,4,5,6-tetrahydropyridazin-3-yl)benzene (0.25 g (7%)), m.p. greater than 250° C. $\nu$ (nujol) 3500, 3310, 3195, 3100, 1753, 1672, 1605, 1342, and 818 cm$^{-1}$ $\delta$ (DMSOd$_6$); 2.46 (4H, t 5,5'—H$_2$), 2.97 (4H, t, 4,4'—H$_2$), 7.89 (4H, s, Phenyl), 10.84 (2H, s, 2×NH).

EXAMPLE 3

1,4-Bis(4-methyl-6-oxo-1,4,5,6-tetrahydropyridazin-3-yl)benzene (a) To initiate reaction several magnesium turnings and one drop of bromoethane were added to a mixture of magnesium powder (7.5 g) in a dry tetrahydrofuran, THF, (20 ml). Steady reflux was maintained by the portionwise addition of a solution of bromoethane (23 ml) in dry THF (50 ml). The solution was stirred under reflux for one hour, treated with a saturated solution of terephthalaldehyde (13.4 g) in THF, the resultant mixture was diluted with THF (100 ml) and stirred under reflux for ½ hour. The reaction mixture was allowed to cool to room temperature and was treated with saturated aqueous ammonium chloride (5 ml), ammonium chloride powder (2 g) and magnesium sulphate. The resultant mixture was stirred for one hour and filtered. The yellow filtrate was evaporated to dryness to yield a solid which was dissolved in a hot mixture of glacial acetic acid and acetone (1:1) and was added portionwise to aqueous chromic acid (1.67M, 150 ml). The solution was allowed to stand at room temperature for 2 days, and was then treated with ethanol (10 ml) and stirred for ½ hour. Water (200 ml) was added and the mixture was extracted with ethyl acetate. The combined ethyl acetate extracts were washed successively with water, dilute aqueous sodium bicarbonate, water and saturated aqueous ammonium chloride, dried (magnesium sulphate) and evaporated to dryness to afford a grey-green oil. Trituration with diethylether petroleum ether (b.p. 40°-60° C.) afforded a solid, which was eluted from a silica column with dichloromethane to afford as white crystals 1,4-dipropionylbenzene (2.4 g) m.p. 98°-101° C.

(b) A mixture of dimethylammonium chloride (5.5 g) and formaldehyde (37% solution, 3.6 ml) was stirred for 5 minutes. Acetic anhydride (26 ml) was added and the resultant mixture was stirred until a clear solution was obtained. 1,4-Dipropionylbenzene (3.8 g) was added and the mixture was stirred at 90° C. for 1½ hours. The resultant solution was evaporated to dryness to afford an orange gum which on trituration with acetone yielded 1,4-bis(3-dimethylamino-2-methylpropionyl)benzene dihydrochloride (5.5 g), m.p. 148°-151° C.

(c) A solution of potassium cyanide (2.07 g) in water (10 ml) was added dropwise at room temperature to a solution of 1,4-bis(3-dimethylamino-2-methylpropionyl)benzene dihydrochloride (5 g) and acetic acid (0.75 ml) in water (30 ml). An orange oil precipitated from the initially clear solution. A further quantity of potassium cyanide (0.85 g) in water (1 ml) was added and the reaction mixture was stirred at 80° C. for 3 hours and then allowed to stand at room temperature for 3 days to afford as a yellow solid, 1,4-bis(3-cyano-2-methylpropionyl)benzene (2.32 g), m.p. 142°-145° C.

(d) A suspension of 1,4-bis(3-cyano-2-methylpropionyl)benzene (1 g) in acetic acid/concentrated hydrochloric acid (1:1, 10 ml) was stirred under reflux for one hour, allowed to stand at room temperature for 16 hours, and evaporated to dryness to afford a residue which was dissolved in dilute aqueous sodium bicarbonate. The solution was filtered and the clear filtrate was acidified to pH 1 with concentrated hydrochloric acid to afford as a creamy yellow solid, 1,4-bis(3-carboxy-2-methylpropionyl)benzene (0.79 g), m.p. 195°-202° C., softens 192° C.

(e) A solution of 1,4-bis(3-carboxy-2-methylpropionyl)benzene (0.75 g) and hydrazine hydrate (2 ml) in water (10 ml) was stirred under reflux for 10 minutes and then allowed to cool. A pale yellow precipitate was collected and was washed with dilute aqueous sodium bicarbonate and water to afford 1,4-bis(4-methyl-6-oxo-1,4,5,6-tetrahydropyridazin-3-yl)benzene (0.24 g), m.p. >300° C., δ (DMSOd$_6$); 1.10 (6H, d), 2.26 (2H, m), 2.71 (2H, m), 3.42 (2H, m), 7.83 (4H, m) and 10.90 (2H, s).

EXAMPLE 4

1,4-Bis(4-methyl-6-oxo-1,6-dihydropyridazin-3-yl)benzene

A mixture of 1,4-bis(4-methyl-6-oxo-1,4,5,6-tetrahydropyridazin-3-yl)benzene (1.41 g), sodium m-nitrobenzenesulphonate (2.20 g) and sodium hydroxide (1 g) in water (100 ml) was stirred under reflux until a clear solution was obtained. Stirring under reflux was continued for one hour and the reaction mixture was cooled to room temperature and filtered. The filtrate was acidified with acetic acid to give a white precipitate, which could not be collected by filtration as it passed through the sinter funnel. The mixture was basified with sodium hydroxide to pH 14 and the resulting solution was then taken to pH 10 with aqueous sodium bicarbonate and allowed to stand at room temperature for 16 hours. A pale yellow solid was collected and was dissolved in dilute aqueous sodium hydroxide. The solution was taken to pH 11 with saturated aqueous ammonium chloride to afford 1,4-bis(4-methyl-6-oxo-1,6-dihydropyridazin-3-yl)benzene (1.02 g), m.p. >250° C.

EXAMPLE 5

1,3-Bis(6-oxo-1,6-dihydropyridazin-3-yl)benzene

A mixture of 1,3-diacetylbenzene (5 g), and glyoxylic acid monohydrate (8.5 g) was stirred and heated at 115° C. for 2 hours. The solid obtained was dissolved in aqueous ammonia (approx. 100 ml) at pH 11 and the solution filtered. The filtrate was treated with hydrazine hydrate (4.5 ml), stirred under reflux for 4 hours and the precipitated solid collected. A suspension of the crude product in acetic acid/concentrated hydrochloric acid (1:1, 30 ml) was stirred under reflux for 40 minutes, and then evaporated to dryness. The residue was dissolved in dilute aqueous sodium hydroxide (250 ml) and the resulting solution was acidified to pH 5 with acetic acid to afford 1,3-bis(6-oxo-1,6-dihydropyridazin-3-yl)benzene (1.78 g), m.p. >250° C., δ (DMSOd$_6$); 6.74 (2H, m), 7.41 (1H, m), 7.52 (2H, m), 7.61 (2H, m), and 7.77 (1H, m).

EXAMPLE 6

6-[4-(4-Methyl-6-oxo-1,4,5,6-tetrahydropyridazin-3-yl)phenyl]pyridazin-3(2H)-one (a) A solution of n-propylbenzene (24 g) and acetyl chloride (14.5 ml) in dichloromethane (80 ml) was added dropwise with cooling to a suspension of anhydrous aluminium chloride (27 g) in dichloromethane (70 ml). The resulting solution was stirred at room temperature for one hour and poured into ice/water (250 ml) containing concentrated hydrochloric acid (10 ml). The organic layer was separated and the aqueous layer was extracted with dichloromethane (3×50 ml). The combined organic fractions were washed with water and saturated aqueous ammonium chloride, dried (magnesium sulphate) and evaporated under reduced pressure to afford a yellow oil which was distilled under reduced pressure to afford 4-n-propyl acetophenone (26 g), b.p. 98° C. at 3 mm Hg.

(b) A mixture of 4-n-propyl acetophenone (20.20 g) and glyoxylic acid monohydrate (11.51 g) was stirred and heated at 110° C. for 3 hours. The semi-solid obtained was dissolved in aqueous ammonia and filtered. The filtrate was treated with hydrazine hydrate (6.5 ml) and stirred under reflux with 4 hours to afford 6-(4-n-propylphenyl)pyridazin-3(2H)-one (11.96 g), m.p.180°-82° C.

(c) A solution of chromium trioxide (6.5 g) in acetic anhydride (29 ml) was added dropwise to a stirred, cooled solution of 6-(4-n-propylphenyl)pyridazin-3(2H)-one (5.11 g) in acetic anhydride (25 ml) containing concentrated sulphuric acid (5 ml). The reaction mixture was stirred at room temperature for 16 hours and then poured into crushed ice (250 ml) to afford 6-(4-propionylphenyl)pyridazin-3(2H)-one (0.78 g), m.p. 202°-205° C.

(d) In a similar manner to Example 3b) a mixture of 6-(4-propionylphenyl)pyridazin-3(2H)-one (2.28 g), formaldehyde (37% solution, 1 ml) and dimethylammonium chloride (1.25 g) in acetic anhydride (8 ml) was stirred at 90° C. for 1½ hours. The cooled solution was poured into dry acetone (150 ml) and was evaporated to dryness under reduced pressure to afford a yellow oil. Trituration with dry acetone afforded 6-[4-(3-dimethylamino-2-methylpropionyl)phenyl]pyridazin-3(2H)-one hydrochloride (2.12 g), as a white solid.

(e) Potassium cyanide (0.32 g) was added to a cooled (5° C.) solution of 6-[4-(3-dimethylamino-2-methylpropionyl)phenyl]pyridazin-3(2H)-one hydrochloride (1.28 g) and acetic acid (0.25 ml) in water (30 ml). The solution was stirred for 2 hours at less than 23° C., then cooled and a further amount of potassium cyanide (0.32 g) was added. After stirring for one hour the temperature was raised to 50° C. and the reaction mixture was stirred for 2 hours to afford 6-[4-(3-cyano-2-methylpropionyl)phenyl]pyridazin-3(2H)-one (0.61 g), m.p. 196°-201° C. (dec), $\nu(C{\equiv}N)$ 2240 cm$^{-1}$.

(f) 6-[4-(3-Cyano-2-methylpropionyl)phenyl]pyridazin-3(2H)-one (0.60 g) in glacial acetic acid/concentrated hydrochloric acid (1:1, 40 ml) was stirred under reflux for 4 hours. The solution was evaporated to dryness and the residue was triturated and warmed with dilute aqueous sodium bicarbonate. On cooling the solution was neutralized with acetic acid and was filtered. Acetic acid (2 ml) and hydrazine hydrate (0.5 ml) were added to the filtrate and the resulting solution was stirred under reflux for 4 hours to afford the crude product (0.58 g). This was dissolved in dilute aqueous sodium hydroxide, filtered and the filtrate was treated with saturated aqueous ammonium chloride. The resultant mixture was heated at less than 60° C. for 2 hours and then allowed to cool to room temperature to afford 6-[4-(4-methyl-6-oxo-1,4,5,6-tetrahydropyridazin-3-yl)phenyl]pyridazin-3(2H)-one (0.42 g), m.p.>250° C., δ (DMSOd$_6$); 1.11 (3H, d), 2.26 (1H, m), 2.72 (1H, m), 3.45 (1H, m), 6.99 (1H, m), 7.91 (4H, m), 8.05 (1H, d), 10.89 (1H, s) and 13.08 (1H, s).

EXAMPLE 7

6-[4-(6-Oxo-1,4,5,6-tetrahydropyridazin-3-yl)phenyl]pyridazin-3(2H)-one

A solution of pyridinium bromide perbromide (0.6 g) in hot acetic acid (50 ml) was added dropwise over 10 minutes to a refluxing mixture of 1,4-bis(6-oxo-1,4,5,6-tetrahydropyridazin-3-yl)benzene (0.5 g) and pyridine (0.3 ml) in glacial acetic acid (100 ml). After addition the clear brown solution was stirred under reflux for 3 hours and was cooled and filtered. The filtrate was concentrated to small volume (ca 10 ml) and was treated with distilled water (100 ml) to yield a brown solid which was collected, washed with ethanol and ether and then dried. The crude material is recrystalised from acetic acid to afford the title compound, m.p. greater than 250° C., H NMR: δ (DMSOd$_6$); 2.45 (2H, t), 2.95 (2H, t), 7.00 (1H, d), 7.88 (4H, m), 8.08 (1H, d) and 10.88 (1H, s).

EXAMPLE 8

Pharmaceutical compositions for oral administration are prepared by combining the following:

|  | % w/w | | |
|---|---|---|---|
| 6-[4-(4-methyl-6-oxo-1,4,5,6-tetrahydropyridazin-3-yl)-phenyl]pyridazin-3(2H)-one | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

What is claimed is:

1. A compound of the formula (I):

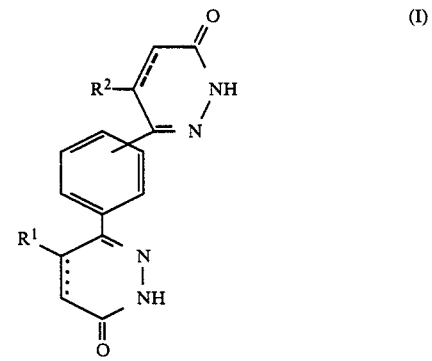

or a pharmaceutically acceptable salt thereof, wherein
R$^1$ is hydrogen or methyl;
R$^2$ is hydrogen or methyl;
.... and ---- represent double or single bonds; and
the benzene ring is para- or meta-substituted.

2. A compound according to claim 1 wherein R$^1$ and/or R$^2$ are hydrogen.

3. A compound according to claim 1 wherein R$^1$ and/or R$^2$ are methyl.

4. A compound according to claim 1 wherein R$^1$ and R$^2$, .... and ---- are such that the molecule is symmetrical.

5. A compound according to claim 1 wherein     is a single bond and R$^1$ is methyl.

6. A compound according to claim 1 wherein     is a single bond and R$^1$ is hydrogen.

7. A compound according to claim 1 wherein     is double bond and R$^2$ is hydrogen.

8. A compound according to claim 1 wherein the benzene ring is para substituted.

9. A compound according to claim 1 which is selected from the group consisting of:

1,4-bis(6-oxo-1,6-dihydropyridazin-3-yl)benzene,
1,4-bis(6-oxo-1,4,5,6-tetrahydropyridazin-3-yl)benzene,
1,4-bis(4-methyl-6-oxo-1,4,5,6-tetrahydropyridazin-3-yl)benzene,
1,4-bis(4-methyl-6-oxo-1,6-dihydropyridazin-3-yl)benzene,
1,3-bis(6-oxo-1,6-dihydropyridazin-3-yl)benzene,
6-[4-(4-methyl-6-oxo-1,4,5,6-tetrahydropyridazin-3-yl)phenyl]pyridazin-3(2H)-one, or
6-[4-(6-oxo-1,4,5,6-tetrahydropyridazin-3-yl)phenyl]-pyridazin-3(2H)-one,
or a pharmaceutically acceptable salt thereof.

10. A compound according to claim 1 which is:
6-[4-(4-methyl-6-oxo-1,4,5,6-tetrahyropyridazin-3-yl)phenyl]pyridazine-3(2H)-one or a pharmaceutically acceptable salt thereof.

11. A compound according to claim 1 which is:
6-[4-(6-oxo-1,4,5,6-tetrahydropyridazin-3-yl)phenyl]-pyridazin-3(2H)-one or a pharmaceutically acceptable salt thereof.

12. A compound according to claim 1 which is:
(R)-6-[4-(4-methyl-6-oxo-1,4,5,6-tetrahydropyridazin-3-yl)phenyl]pyridazin-3(2H)-one or a pharmaceutically acceptable salt thereof.

13. A method for effecting phosphodiesterase (type III) inhibition in a host in need thereof by administration of a non-toxic but effective amount of a compound according to claim 1.

14. A pharmaceutical composition which comprises a compound according to claim 1 and a pharmaceutically acceptable carrier.

15. A pharmaceutical composition which comprises a compound according to claim 10 and a pharmaceutically acceptable carrier.

16. A pharmaceutical composition which comprises a compound according to claim 11 and a pharmaceutically acceptable carrier.

17. A pharmaceutical composition according to claim 14 in unit dose form adapted for oral administration.

18. A method for stimulating cardiac activity in a host in need thereof by administration of a non-toxic but effective amount of a compound according to claim 1.